(12) United States Patent
Kuramochi

(10) Patent No.: US 11,241,341 B2
(45) Date of Patent: Feb. 8, 2022

(54) ABSORBENT ARTICLE

(71) Applicant: DAIO PAPER CORPORATION, Ehime (JP)

(72) Inventor: Mihoko Kuramochi, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 516 days.

(21) Appl. No.: 16/317,965

(22) PCT Filed: Jul. 20, 2017

(86) PCT No.: PCT/JP2017/026287
§ 371 (c)(1),
(2) Date: Jan. 15, 2019

(87) PCT Pub. No.: WO2018/021144
PCT Pub. Date: Feb. 1, 2018

(65) Prior Publication Data
US 2020/0121518 A1  Apr. 23, 2020

(30) Foreign Application Priority Data
Jul. 27, 2016 (JP) .............................. JP2016-147874

(51) Int. Cl.
  *A61F 13/47* (2006.01)
  *A61F 13/472* (2006.01)
  *A61F 13/475* (2006.01)

(52) U.S. Cl.
  CPC ...... *A61F 13/47245* (2013.01); *A61F 13/475* (2013.01); *A61F 2013/4706* (2013.01)

(58) Field of Classification Search
  CPC .......... A61F 13/47236; A61F 13/47245; A61F 13/475; A61F 2013/4706
  See application file for complete search history.

(56) References Cited

U.S. PATENT DOCUMENTS 7,056,311 B2 * 6/2006 Kinoshita ........... A61F 13/4753
                                                604/385.03
9,114,044 B2 * 8/2015 Yoshiba ................ A61F 13/472
(Continued)

FOREIGN PATENT DOCUMENTS

CN        101878010           11/2010
JP        2010082061 A  *  4/2010   ........... A61F 13/475
(Continued)

OTHER PUBLICATIONS

International Search Report for PCT/JP2017/026287 dated Sep. 5, 2017.
Chinese Office Action for 201780044779.9 dated Nov. 4, 2020.

*Primary Examiner* — Catharine L Anderson
(74) *Attorney, Agent, or Firm* — IPUSA, PLLC

(57) ABSTRACT

An absorbent article includes a body and a hip holding portion. The body has a shape having a predetermined length in a front-rear direction and a predetermined width in a direction perpendicular to the front-rear direction. The hip holding portion includes a side region protruding from a rear side portion of the body and a rear region protruding from the rear end of the body, and includes a first protruding portion including a portion where the width of the body from a centerline in the front-rear direction is largest, a first depressed portion forward of and adjacent to the first protruding portion, and a second protruding portion forward of and adjacent to the first depressed portion in the side region. The width of the second protruding portion from the centerline is smaller than or equal to the smallest width of the first depressed portion from the centerline.

8 Claims, 3 Drawing Sheets

(56) References Cited

U.S. PATENT DOCUMENTS

2010/0305539 A1 12/2010 Odoi
2018/0369026 A1* 12/2018 Shima .................... A61F 13/56

FOREIGN PATENT DOCUMENTS

| JP | 4476611 | 6/2010 |
| JP | 2011-172658 | 9/2011 |
| JP | 2014-036832 | 2/2014 |
| JP | 2014-144140 | 8/2014 |
| JP | 2016-119988 | 7/2016 |

* cited by examiner

ABSORBENT ARTICLE

TECHNICAL FIELD

The present invention relates to absorbent articles.

BACKGROUND ART

Conventionally, as absorbent articles such as panty liners, sanitary napkins, and incontinence pads, those having an absorber provided between a liquid-permeable top sheet and a liquid-impermeable bottom sheet are known.

Furthermore, in recent years, it has been known to provide an extension portion by elongating and widening an absorbent article from both sides in the rear to the rear end, in order to prevent leakage of a body fluid from the back or diagonal back of the absorbent article.

For example, Patent Document 1 discloses an absorbent article including a hip flap portion that includes a first narrowed portion, a first flap portion, and a second flap portion, where the first flap portion is positioned rearward of the first narrowed portion and protrudes widthwise outward relative to the first narrowed portion, the first flap portion includes a portion where the hip flap portion is widest, and the second flap portion is positioned forward of the first narrowed portion and protrudes widthwise outward relative to the first narrowed portion.

Furthermore, Patent Document 2 discloses a sanitary napkin including rear flaps that are greater in length than fold-back flap portions and in which a starting point at which a half width in a lateral direction from a longitudinal centerline to an edge starts to increase rearward from a portion where the half width is minimized is provided rearward of the fold-back flap portions, where the rear flaps include respective front spreading portions, intermediate portions having edges parallel to the longitudinal centerline, and rear converging portions.

PRIOR ART DOCUMENT

Patent Document

Patent Document 1: Japanese Laid-Open Patent Publication No. 2014-36832
Patent Document 2: Japanese Patent No. 4476611

SUMMARY OF THE INVENTION

Problems to be Solved by the Invention

According to the absorbent article of Patent Document 1, however, a flap portion positioned forward of the first flap portion is likely to be turned up, and the turned-up portion may touch skin to give a feeling of strangeness.

Furthermore, the shape of the rear flap portion of the sanitary napkin of Patent Document 2 cannot flexibly deform along the roundness of the buttocks. Therefore, the rear flap portion cannot fit the buttocks well, and when there is a gap between the flap portion and the buttocks, a body fluid may leak from the gap.

In view of the above-described point, the present invention has an object of providing an absorbent article that can fit well along the shape of the buttocks and prevents its hip holding portion from being turned up to provide a good fit.

Means for Solving the Problems

To solve the above-described problems, according to a first embodiment of the present invention, an absorbent article includes a body including a liquid-permeable top sheet, a liquid-impermeable bottom sheet, and an absorber provided between the top sheet and the bottom sheet, and a hip holding portion. The body has a shape having a predetermined length in a front-rear direction and a predetermined width in a direction perpendicular to the front-rear direction. The hip holding portion includes a side region protruding from a rear side portion of the body and a rear region protruding from the rear end of the body, and includes a first protruding portion including a portion where the width of the body from a centerline in the front-rear direction is largest, a first depressed portion forward of and adjacent to the first protruding portion, and a second protruding portion forward of and adjacent to the first depressed portion in the side region. The width of the second protruding portion from the centerline is smaller than or equal to the smallest width of the first depressed portion from the centerline.

According to the above-described first embodiment, the hip holding portion includes the first protruding portion including the portion where the width from the centerline in the front-rear direction is largest, the first depressed portion forward of and adjacent to the first protruding portion, and the second protruding portion forward of and adjacent to the first depressed portion in the side region. Therefore, when the hip holding portion is applied along the buttocks in attaching the absorbent article, the first protruding portion and the second protruding portion can deform independent of each other without affecting each other because there is the first depressed portion between the first protruding portion and the second protruding portion. This enables the hip holding portion to deform along the curved surface (roundness) of the buttocks, thus making it possible to improve the fit of the hip holding portion to a body.

The second protruding portion, however, is formed forward of the first protruding portion. That is, the second protruding portion is formed at a position closer to the base of the legs when attached, and is therefore susceptible to a force due to the movement of the legs. Therefore, in the second protruding portion, (part of) the protruding portion may be turned up to be folded toward skin or underwear or to generate small wrinkles or twists (which may be hereinafter referred to as "turn-up or twist").

By causing the width of the second protruding portion from the centerline to be smaller than or equal to the smallest width of the first depressed portion from the centerline, however, the second protruding portion can be less likely to be turned up. In addition, because there is the first depressed portion between the first protruding portion and the second protruding portion as described above, the effect or function that the first protruding portion and the second protruding portion deform independent of each other is maintained. Therefore, it is possible to reduce a feeling of strangeness caused by the contact of a turned-up portion with the body while maintaining the fit of the hip holding portion to the body, so that it is possible to provide an absorbent article that provides a good fit.

According to a second embodiment of the present invention, the radii of curvature of the first protruding portion and the second protruding portion are greater than the radius of curvature of the first depressed portion.

According to the above-described second embodiment, by causing the radii of curvature of the first protruding portion and the second protruding portion to be greater than the radius of curvature of the first depressed portion, the hip holding portion is more likely to deform along the roundness of the buttocks, so that it is possible to further improve the fit of the hip holding portion to the body.

According to a third embodiment of the present invention, the hip holding portion includes a third protruding portion, and a third depressed portion and a fourth depressed portion adjacent to the third protruding portion on both sides thereof in the rear region, and the apex of the third protruding portion is positioned on the centerline.

According to the above-described third embodiment, the apex of the third protruding portion is positioned on the centerline in the front-rear direction in the rear region. Therefore, even in the case where a body fluid runs along the fissure (cleft) of the buttocks when sleeping on the back, it is possible to successfully prevent leakage of the body fluid from the rear.

According to a fourth embodiment, the radius of curvature of the third protruding portion is smaller than the radius of curvature of the third depressed portion and the radius of curvature of the fourth depressed portion.

According to the above-described fourth embodiment, by causing the radius of curvature of the third protruding portion to be smaller than the radius of curvature of the third depressed portion and the radius of curvature of the fourth depressed portion, the third protruding portion is likely to deform along the centerline in the front-rear direction. Therefore, the hip holding portion is likely to enter the cleft of the buttocks, thus making it possible to reliably absorb a body fluid running along the fissure of the buttocks.

According to a fifth embodiment of the present invention, a wing portion is included on a front side portion of the body, and the outline of an intermediate portion between the wing portion and the hip holding portion is free of a depression and a protrusion.

According to the above-described fifth embodiment, by causing the intermediate portion between the wing portion and the hip holding portion to be free of a depression and a protrusion, it is possible to prevent the turn-up of a side portion due to depressions and protrusions, which is likely to occur around the legs.

According to a sixth embodiment of the present invention, the angle between a virtual line and the centerline is 15° or greater and 22° or less, where the virtual line is drawn from a point at the rear end of the wing portion where the absorbent article is narrowest to contact the outermost outline of the outer shape of the hip holding portion.

According to the above-described sixth embodiment, by causing the angle between the virtual line and the centerline to be 15° or greater and 22° or less, where the virtual line is drawn from the point at the rear end of the wing portion where the absorbent article is narrowest to contact the outermost outline of the outer shape of the hip holding portion, it is possible to reduce the turn-up and twist of a side portion of the absorbent article, so that an absorbent article providing a good fit without causing a feeling of strangeness around the legs is provided.

Effects of the Invention

According to an embodiment of the present invention, an absorbent article that can fit well along the shape of the buttocks and prevents its hip holding portion from being turned up to provide a good fit is provided.

EMBODIMENT OF THE INVENTION

An embodiment of the present invention is described below with reference to the drawings.

Figure 1:
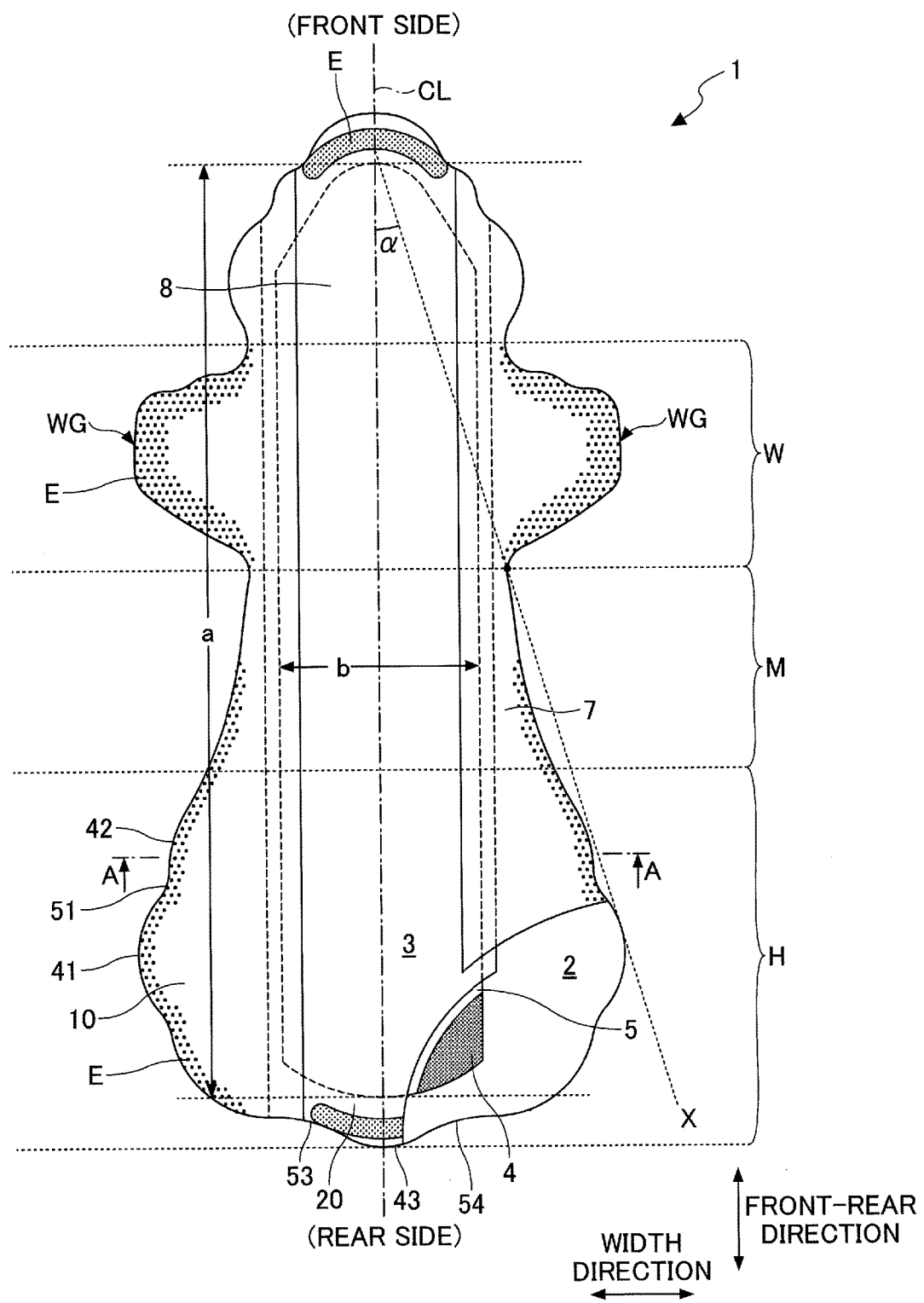
FIG. 1 is a partial cutaway view of an absorbent article according to an embodiment of the present invention.
Figure 2:
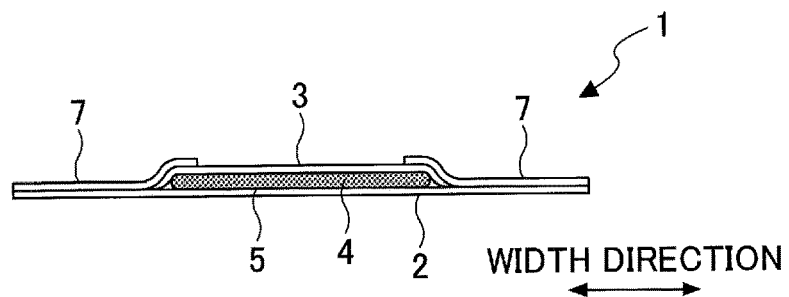
FIG. 2 is a cross-sectional view of the absorbent article according to the embodiment of the present invention, taken along the line A-A.

As illustrated in FIGS. 1 and 2, an absorbent article 1 includes a body (absorbent article body) 8 that includes a liquid-impermeable bottom sheet 2, a liquid-permeable top sheet 3, and an absorber 4 provided between these sheets 2 and 3. To maintain the shape of the absorber 4, the absorber 4 may be enveloped in an enveloping sheet 5 made of crepe paper, nonwoven fabric or the like. As illustrated in FIG. 1, the absorbent article 1 further includes a hip holding portion H as described below and a wing portion W including wings WG.

When in use, the absorbent article 1 is attached to underwear such that the wing portion W faces forward and the hip holding portion H faces rearward. As illustrated in FIG. 1, as a whole, the body 8 is elongated to have a predetermined length a in the front-rear direction, and has a fixed width b in a direction perpendicular to the front-rear direction. The absorbent article 1 has a substantially line-symmetric shape with respect to a centerline CL extending in the front-rear direction.

At the front and the rear end edge of the absorber 4, the outer edge of the bottom sheet 2 and the outer edge of the top sheet 3 are joined by an adhesive such as a hot glue or bonding means such as heat sealing or ultrasonic sealing. Furthermore, side nonwoven fabrics 7 are provided one on each side of the top sheet along the front-rear direction (longitudinal direction). The side nonwoven fabrics 7 partially protrude sideways relative to the body 8, and are stacked on and joined by an adhesive such as a hot glue or bonding means such as heat sealing or ultrasonic sealing to the bottom sheet 2 that also protrudes sideways, thereby forming a side region 10 of the hip holding portion H and the wings WG.

A sheet material that is at least impervious to water, such as a sheet of an olefin resin such as polyethylene or polypropylene, may be used as the bottom sheet 2. A laminate nonwoven fabric that is a laminate of a polyethylene sheet or the like and a nonwoven fabric, and a laminated sheet of nonwoven fabrics that substantially ensures liquid impermeability by interposing a waterproof film may be used. Furthermore, in light of prevention of stuffiness, it is further desired to use one with moisture permeability. As such a water-impervious and moisture-permeable sheet material, a microporous sheet obtained by forming a sheet by dissolving and mixing inorganic filler in an olefin resin such as polyethylene or polypropylene, and thereafter stretching the sheet in one axial or two axial directions, may be used.

The top sheet 3 is a liquid-permeable sheet that allows quick passage of a body fluid such as menstrual blood, vaginal discharge, or urine. As the top sheet 3, a porous or nonporous nonwoven fabric or a porous plastic sheet is preferably used. Examples of fiber materials of the nonwoven fabric include synthetic fibers of olefin such as polyethylene or polypropylene, polyester, or polyamide; regenerated fibers such as rayon and cuprammonium rayon; mixed fibers of these; and natural fibers such as cotton, which may be used alone or in any combination. Furthermore, methods of processing the nonwoven fabric include spunlacing, spunbonding, thermal bonding, melt blowing, and needle punching. Of these processing methods, spunlacing is preferable in being capable of manufacturing a nonwoven fabric with good flexibility, spunbonding is preferable in being capable of manufacturing a nonwoven fabric with good drapability, and thermal bonding is preferable in being capable of manufacturing a lofty, soft nonwoven fabric. Furthermore, composite fibers such as sheath-core fibers having a high-melting-point fiber as a core and a low-melting-point fiber as a sheath, side-by-side fibers, and split fibers may be used.

The absorber 4 interposed between the bottom sheet 2 and the top sheet 3, whose material is not limited as long as it can absorb and hold a body fluid, preferably includes cotton pulp and a water absorptive polymer. Usable water absorptive polymers include superabsorbent polymers (SAPs), superabsorbent fibers (SAFs), and their mixtures. Examples of pulp include those made of cellulose fibers, such as chemical pulp and dissolving pulp obtained from wood, and those made of artificial cellulose fibers such as rayon and acetate. While hardwood materials and softwood materials are used as raw materials of chemical pulp, softwood materials are suitably used because of long fiber length.

Synthetic fibers may be mixed into the absorber 4. Usable synthetic fibers include polyolefins such as polyethylene and polypropylene, polyesters such as polyethylene terephthalate and polybutylene terephthalate, polyamides such as nylon, and their copolymers, of which two may be used in mixture. Furthermore, composite fibers such as sheath-core fibers having a high-melting-point fiber as a core and a low-melting-point fiber as a sheath, side-by-side fibers, and split fibers may also be used. Hydrophobic fibers subjected to surface treatment with a hydrophilizing agent to be provided with affinity for body fluids may also be used.

The thickness of the absorber 4 preferably ranges from approximately 0.5 to 25 mm. The absorber 4 does not have to be uniform in thickness in its entirety, and may include a bulging portion corresponding to where a body fluid is discharged. The absorber 4 is preferably manufactured by fiber stacking or air laying.

As the side nonwoven fabrics 7, a water-repellant nonwoven fabric or a hydrophilized nonwoven fabric may be used. For example, in the case of improving an anti-permeation effect against menstrual blood, vaginal discharge or the like, or the feel of texture, it is preferable to use a water-repellant nonwoven fabric coated with a silicon, paraffin, or alkyl chromic chloride water repellent. In the case of improving the capability of absorbing menstrual blood or the like in the hip holding portion H, it is preferable to use a hydrophilized nonwoven fabric as the material of a nonwoven fabric. A preferable type of nonwoven fabric is an air through nonwoven fabric that is less likely to develop folds, wrinkle-resistant, and soft.

As illustrated in FIG. 1, in order to join the side nonwoven fabrics 7 and the bottom sheet 2 and increase stiffness, an embossed portion E provided with dot embossings or embossings having a predetermined shape may be provided in a predetermined area on the outer edges of the side region 10 of the hip holding portion H and the wings WG of the wing portion W.

According to this embodiment, the absorbent article 1 includes the body 8, which includes the liquid-permeable top sheet 3, the liquid-impermeable bottom sheet 2, and the absorber 4 provided between these sheets 2 and 3, and the hip holding portion H.

Figure 5:
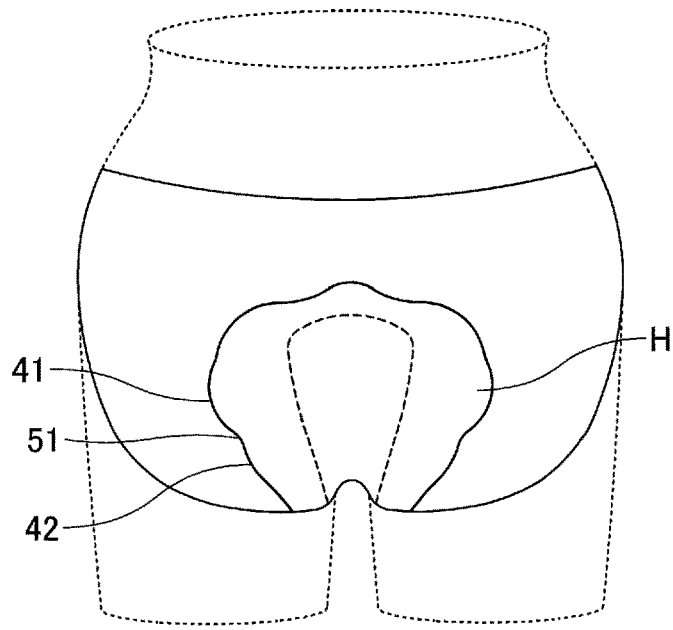
FIG. 5 is a model diagram illustrating the absorbent article according to the embodiment of the present invention that is worn.

The hip holding portion H is an area extension part formed by increasing the length and width of a part of the absorbent article from both sides in the rear to the rear end, and has the function of preventing leakage of a body fluid from the back or diagonal back of the absorbent article 1 by being fixed to the buttocks inner side of underwear when attached to the underwear as illustrated in FIG. 5. As illustrated in FIG. 1, the hip holding portion H includes a flap-shaped portion in which the side nonwoven fabrics 7 and the bottom sheet 2 are layered, extending from both sides in the rear to the rear end of the body 8 of the absorbent article 1.

The hip holding portion H includes the side region 10 protruding from a rear side portion of the body 8 and a rear region 20 protruding from the rear end of the body 8. The side region 10 of the hip holding portion H includes a region formed mainly by sticking the bottom sheet 2 and the side nonwoven fabrics 7 together, and the rear region 20 includes a region formed mainly by sticking the bottom sheet 2 and the top sheet 3 together.

Preferably, the side region 10 and the rear region 20 of the hip holding portion H do not include the absorber 4 and are thinner than the body 8. This makes it possible to move more flexibly than the body 8. It is also possible, however, to layer an absorber thinner than the absorber 4 used in the body 8 between the bottom sheet 2 and the side nonwoven fabrics 7 in the hip holding portion H.

The hip holding portion H may be a portion starting from a position corresponding to the rear end of the crotch of underwear when attached to extend to the rear end of the absorbent article 1. In the case of FIG. 1, the hip holding portion H may be a portion extending in the front-rear direction from the position of the front terminal end of a second protruding portion 42 to the rear end of the absorbent article 1. For example, the length of the hip holding portion H in the front-rear direction is preferably 50 mm or more and 200 mm or less, and more preferably, 80 mm or more and 180 mm or less. Furthermore, the overall length of the absorbent article 1 may be 200 mm or more and 450 mm or less, and the length of the hip holding portion H in the front-rear direction is preferably 10% or more and 50% or less of this overall length. The hip holding portion H includes a portion where the width of the absorbent article 1 is largest, and the width is preferably 120 mm or more and 230 mm or less.

Furthermore, the periphery (outline) of the hip holding portion H includes depressions and protrusions. For example, as illustrated in FIG. 1, the hip holding portion H includes a first protruding portion 41 including a portion where the width of the body from the centerline 8 in the front-rear direction is largest, a first depressed portion 51 forward of and adjacent to the first protruding portion 41, and the second protruding portion 42 forward of and adjacent to the first depressed portion 51 in the side region 10.

Effects according to the formation of depressed and protruding portions in the periphery of the hip holding portion H are described below.

The hip holding portion H as a whole has a planar shape. When this planar hip holding portion H is applied to the buttocks, which have a curved surface shape, a peripheral region of the hip holding portion H in particular may twist to generate wrinkles because of a difference between the planar shape and the curved surface shape. The size and the number of wrinkles to be generated are related to the overall area of the hip holding portion H and the curved surface shape of the buttocks. If the above-described protruding and depressed portions are not formed in the periphery of the hip holding portion H, large wrinkles may be generated at multiple points in the peripheral region of the hip holding portion H. Such large wrinkles touch the skin of the buttocks to give a feeling of strangeness. In particular, in the case of being seated on a chair for a long time or sleeping on the back at night, part of body weight is applied to the buttocks, so that a feeling of strangeness or an uncomfortable feeling increases accordingly. Furthermore, the wrinkles may further increase in size because of a change in the magnitude of body weight applied to the buttocks due to a change in a sleeping posture or a change in a sitting posture, or a change in the contact state of the buttocks and the hip holding portion H. Furthermore, in the case of sleeping on the back or on the side at night, a body fluid is likely to leak outside from a gap caused by such wrinkles.

In contrast, according to this embodiment, the outer shape of the hip holding portion H includes a depressed portion between two protruding portions. Therefore, for example, even when a force to generate wrinkles acts on the first protruding portion 41, the presence of the first depressed portion 51 prevents the force generated in the first protruding portion 41 from being transmitted to the second protruding portion 42. Therefore, the force generated in the first protruding portion 41 remains in the area of the first protruding portion 41. The same applies to the case where a force to generate wrinkles acts on the second protruding portion 42. Thus, the first protruding portion 41 and the second protruding portion 42 can deform independent of each other without affecting each other. Furthermore, even when wrinkles are generated, the wrinkles are prevented from increasing in size.

Therefore, when the hip holding portion H is applied along the curved surface of the buttocks in attaching the absorbent article, it is possible to deform the hip holding portion H along the curved surface of the buttocks. This makes it possible to improve the fit of the hip holding portion H to the buttocks.

According to the depicted embodiment, the first protruding portion 41, the first depressed portion 51, and the second protruding portion 42 are provided in the side region 10 of the hip holding portion H. The number and the shapes of protruding portions and depressed portions, however, are not limited to the depicted example. For example, two to five protruding portions and one to five depressed portions may be provided in the side region 10 of the hip holding portion H.

Figure 3:
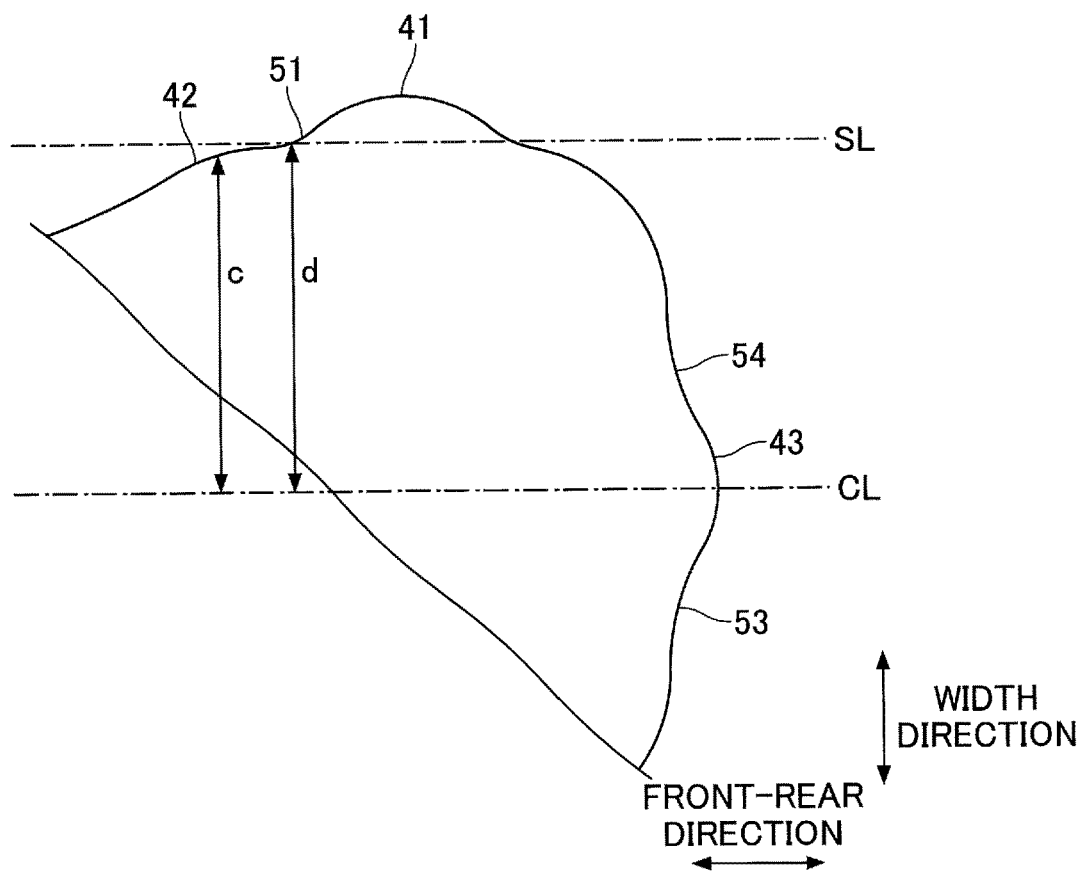
FIG. 3 is a partial blown-up view of a hip holding portion according to the embodiment of the present invention.

Furthermore, as illustrated in FIG. 3, in the side region 10 of the hip holding portion H, a width c of the second protruding portion 42 from the centerline CL is smaller than or equal to a smallest width d of the first depressed portion 51 from the centerline CL. That is, when a reference line SL parallel to the centerline CL in the front-rear direction is drawn from a position where the width of the first depressed portion 51 is smallest (a point of transition from the outline of the first depressed portion 51 to the outline of the second protruding portion 42), the second protruding portion 42 does not protrude outward from the reference line SL.

When the tangent direction of a curved line continuing from the outline of the first depressed portion 51 to the outline of the second protruding portion 42 continuously changes, the point of transition from the outline of the first depressed portion 51 to the outline of the second protruding portion 42 becomes an inflection point of the curved line. When a change in the tangent direction of the curved line is discontinuous, the vicinity of the point of transition may be approximated by a smooth curved line.

As illustrated in FIGS. 1 and 3, the second protruding portion 42 is formed forward of the first protruding portion 41, that is, the second protruding portion 42 is formed at a position closer to the base of the legs when attached. Therefore, the second protruding portion 42 is susceptible to a force due to the movement of the legs. Therefore, as the width of the second protruding portion 42 from the centerline CL becomes greater than the smallest width of the first depressed portion 51 from the centerline CL (as the second protruding portion 42 protrudes more outward from the reference line SL), the second protruding portion 42 becomes more susceptible to a force due to the movement of the legs. Thus, the second protruding portion 42 is likely to be turned up or twisted to a large extent. In contrast, according to the present invention, the second protruding portion 42 is provided relatively gently, and does not excessively protrude widthwise outward. Therefore, even when subjected to a force due to the movement of the legs, the second protruding portion 42 is less likely to be turned up or twisted. Furthermore, there is the first depressed portion 51 between the second protruding portion 42 and the first protruding portion 41. Therefore, even when a force to generate wrinkles is generated on the first protruding portion 41 side, it is possible to maintain the above-described function of preventing the force from being transmitted to the second protruding portion 42 side. Accordingly, it is possible to reduce a feeling of strangeness caused by the contact of a turned-up portion or twisted portion with the skin surface of the buttocks while maintaining the fit of the hip holding portion H to the curved surface of the buttocks, so that it is possible to provide an absorbent article that provides a good fit. Furthermore, the configuration of the hip holding portion H of this embodiment can fit to different curved surface shapes of the buttocks of users. Therefore, it is possible to provide users of various body types with an absorbent article that provides a good fit.

Even in the case of providing three or more protruding portions and two or more depressed portions in the side region 10 of the hip holding portion H, the relationship between a depressed portion and a protruding portion forward of the depressed portion may be such that the width of the protruding portion from a centerline is smaller than or equal to the smallest width of the depressed portion from the centerline.

As described above, the absorbent article 1 according to this embodiment fits well to a body, in particular, to the buttocks, and successfully prevents a protruding portion of the hip holding portion H from being turned up or twisted. Therefore, a gap is less likely to be formed between the hip holding portion H and the buttocks. Accordingly, it is possible to effectively prevent leakage of a body fluid from such a gap.

In the side region 10 of the hip holding portion H, the radii of curvature of the first protruding portion 41 and the second protruding portion 42 are preferably greater than the radius of curvature of the first depressed portion 51. This makes it possible to make the narrowing of the first depressed portion 51 relatively deeper, so that the first depressed portion 51 acts like a cut. Therefore, with the first protruding portion 41 serving as a base point, the first protruding portion 41 and the second protruding portion 42 are likely to independently deform to fit more to the curved surface of the buttocks. Accordingly, the hip holding portion H is more likely to deform along the curved surface of the buttocks, so that it is possible to further improve the fit of the hip holding portion H to the body.

Figure 4:
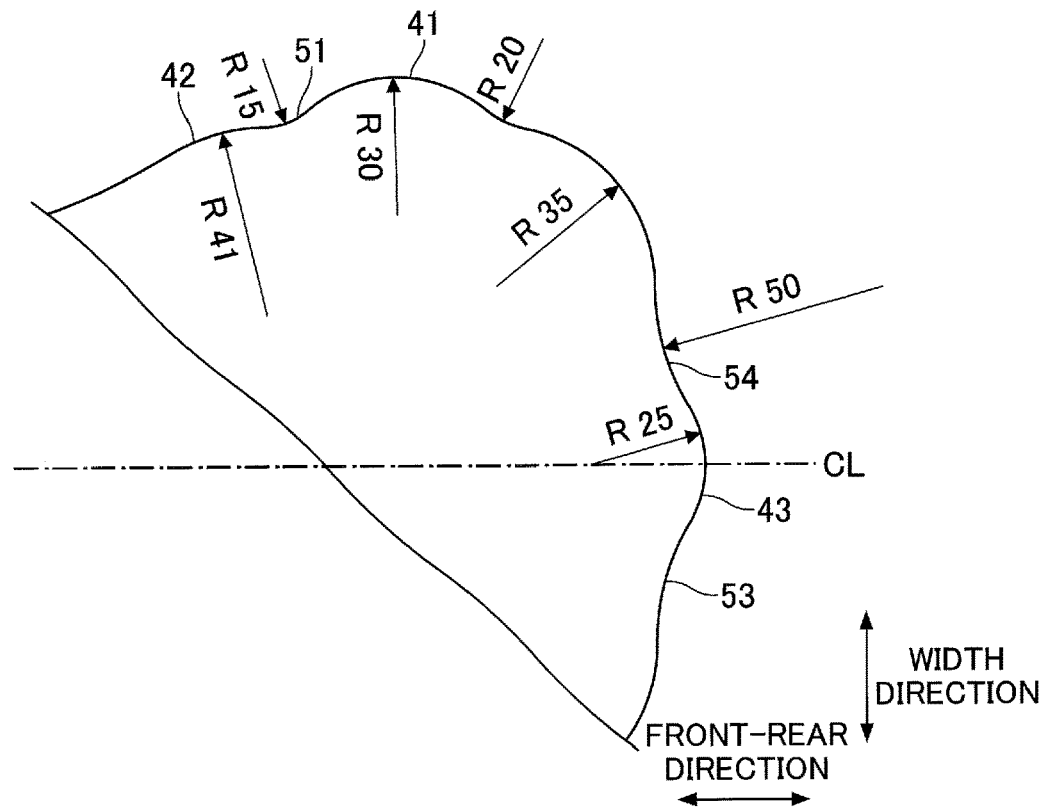
FIG. 4 is a partial blown-up view of the hip holding portion according to the embodiment of the present invention.

The radii of curvature (unit: mm) of the first protruding portion 41, the second protruding portion 42, and the first depressed portion 51 provided in the side region 10 of the hip holding portion H are not limited, but are preferably within approximately ±10 mm of the values of radii of curvature shown as examples in FIG. 4. More preferably, depending on the shapes and size of the body 8 and the hip holding portion H, the above-described radii of curvature may be such that the radius of curvature R of the first protruding portion 41 is 25 to 35 mm, the radius of curvature R of the second protruding portion 42 is 36 to 46 mm, and the radius of curvature R of the first depressed portion 51 is 10 to 20 mm.

Furthermore, preferably, in the rear region 20, the hip holding portion H includes a third protruding portion, and a third depressed portion and a fourth depressed portion adjacent to the third protruding portion on both sides, and the apex of the third protruding portion is positioned on the centerline CL, as illustrated in FIG. 1.

In the case of using the absorbent article during sleeping at night, a body fluid is likely to run rearward along the cleft of the buttocks because a wearer is often in a supine position. When the apex of the third protruding portion 43 is positioned on the centerline CL extending in the front-rear direction, however, the hip holding portion H protrudes to extend on the extension of the cleft of the buttocks. Therefore, it is possible to successfully catch a body fluid running along the cleft of the buttocks.

As illustrated in FIG. 4, the radius of curvature of the third protruding portion is smaller than the radius of curvature of the third depressed portion and the radius of curvature of the fourth depressed portion. As a result, the third protruding portion 43 is likely to deform along the centerline CL extending in the front-rear direction. That is, the rear of the hip holding portion H is likely to bulge with the centerline CL serving as a peak. Therefore, the hip holding portion H is likely to enter the cleft of the buttocks to allow the body 8 to fit tightly to the cleft of the buttocks, thus making it possible to quickly absorb a body fluid running along the cleft of the buttocks. Accordingly, the absorbent article 1 according to an embodiment of the present invention can be suitably used as an article worn in a position where a body fluid is likely to run along the cleft of the buttocks, that is, in a supine position, such as a night-time sanitary napkin.

The radii of curvature (unit: mm) of the third protruding portion 43, the third depressed portion 53, and the fourth depressed portion 54 provided in the rear region 20 of the hip holding portion H are not limited, but are preferably within approximately ±10 mm of the values of radii of curvature shown as examples in FIG. 4. More preferably, depending on the shapes and size of the body 8 and the hip holding portion H, the above-described radii of curvature may be such that the radius of curvature R of the third protruding portion 43 is 20 to 30 mm, and the radius of curvature of the third depressed portion 53 and the radius of curvature R of the fourth depressed portion 54 are both 45 to 55 mm.

The absorbent article 1 preferably includes the wing portion W including the two wings WG provided one on each side of a front side portion of the body 8. The wing portion W may be a portion from the front terminal end to the rear terminal end of the wings WG (from the front end to the rear end of the base of the wings WG) in the front-rear direction. As described above, the wings WG are formed by layering the side nonwoven fabrics 7 and the bottom sheet 2. The wings WG are portions that are folded outward of underwear in such a manner as to be wrapped around the crotch of the underwear to fix the absorbent article 1 to the underwear, when attached.

Preferably, in the front-rear direction, the outer shape of an intermediate portion M positioned between the two extending portions of the wing portion W and the hip holding portion H includes no depressions or projections. This intermediate portion M is a region that contacts leg surfaces when the absorbent article 1 is worn. That is, the intermediate portion M is a region that is most likely to be affected by a force from the legs in the absorbent article 1. Therefore, if the outline of this intermediate portion M includes depressions and protrusions, a turn-up is more likely to occur particularly in protruding portions because of the movement of the skin of the femoral base. Therefore, by not providing depressions or protrusions in the intermediate portion M, it is possible to prevent the sides of the absorbent article 1 from being turned up, so that it is possible to further improve the fit of the absorbent article 1.

The outline of the intermediate portion M may be rectilinear as long as no depressions or protrusions are formed. Furthermore, as a whole, the outline may be a smooth convex curving outward relative to the centerline or a smooth concave toward the centerline. In view of improvement of a fit, however, the outline preferably includes a concave.

As illustrated in FIG. 1, the intermediate portion M may be a region from the rear terminal end of the wings WG to the front terminal end of the second protruding portion 42.

The ratio of the length of the intermediate portion M and the length of the hip holding portion H in the front-rear direction preferably ranges from 1:4 to 2:3. By setting the ratio to 1:4 or more, the depressions and protrusions of the hip holding portion H are prevented from going inside the thighs, so that it is possible to prevent the turn-up of the outer shape. By setting the ratio to 2:3 or less, it is possible to ensure a sufficient length of the hip holding portion H.

As illustrated in FIG. 1, the hip holding portion H of this embodiment has a shape in which an area extension part continuing from the somewhat long-bodied intermediate portion M is shifted rearward, and is pyriform to hold the buttocks (hip). That is, an angle α between a straight line (virtual line) X and the centerline CL in the front-rear direction is preferably 15° or greater and 22° or less, and more preferably, 16° or greater and 20° or less, where the straight line X is the outermost line in the width direction among the lines that pass a point where the width of the absorbent article 1 is smallest (the rear terminal end of the wings WG) and touch the hip holding portion H. Furthermore, neither the intermediate portion M nor the hip holding portion H includes a portion that protrudes widthwise outward of the straight line X. Because of this shape, an absorbent article that provides a good fit without causing a feeling of strangeness particularly around the legs is provided.

The present application is based on and claims priority to Japanese patent application No. 2016-147874, filed on Jul. 27, 2016, the entire contents of which are hereby incorporated herein by reference.

DESCRIPTION OF THE REFERENCE NUMERALS 1 absorbent article
2 bottom sheet 3 top sheet
4 absorber
5 enveloping sheet
7 side nonwoven fabric
10 side region
20 rear region
41 first protruding portion
42 second protruding portion
43 third protruding portion
51 first depressed portion
53 third depressed portion
54 fourth depressed portion
H hip holding portion
W wing portion
E embossed portion
WG wing
CL front-rear direction centerline
SL reference line
X straight line (virtual line)

The invention claimed is:

1. An absorbent article including a body and a hip holding portion, the body including a liquid-permeable top sheet, a liquid-impermeable bottom sheet, and an absorber provided between the top sheet and the bottom sheet, wherein:
the body has a shape having a predetermined length in a front-rear direction and a predetermined width in a direction perpendicular to the front-rear direction,
the hip holding portion includes a side region protruding from a rear side portion of the body and a rear region protruding from a rear end of the body, the hip holding portion including a first protruding portion, a first depressed portion, and a second protruding portion in the side region, the first protruding portion including a portion where a width of the body from a centerline in the front-rear direction is largest, the first depressed portion being immediately forward of the first protruding portion, the second protruding portion being immediately forward of the first depressed portion, and
a largest width of the second protruding portion from the centerline is smaller than or equal to a smallest width of the first depressed portion from the centerline.

2. The absorbent article as claimed in claim 1, wherein radii of curvature of the first protruding portion and the second protruding portion are greater than a radius of curvature of the first depressed portion.

3. The absorbent article as claimed in claim 1, wherein the hip holding portion includes a third protruding portion, a third depressed portion, and a fourth depressed portion in the rear region, the third depressed portion and the fourth depressed portion being adjacent to the third protruding portion on both sides thereof, and an apex of the third protruding portion is positioned on the centerline.

4. The absorbent article as claimed in claim 3, wherein a radius of curvature of the third protruding portion is smaller than a radius of curvature of the third depressed portion and a radius of curvature of the fourth depressed portion.

5. The absorbent article as claimed in claim 1, comprising:
a wing portion on a front side portion of the body,
wherein an outline of an intermediate portion between the wing portion and the hip holding portion is free of a depression and a protrusion.

6. The absorbent article as claimed in claim 5, wherein an angle between a virtual line and the centerline is 15° or greater and 22° or less, the virtual line being drawn from a point at a rear end of the wing portion where the absorbent article is narrowest to contact an outermost outline of an outer shape of the hip holding portion.

7. The absorbent article as claimed in claim 1, further comprising:
a wing portion on a front side portion of the body, and
an intermediate portion between the wing portion and the hip holding portion,
wherein the outline of the intermediate portion is rectilinear or concave toward the centerline.

8. The absorbent article as claimed in claim 1, wherein the second protruding portion is a single protruding portion forward of the first protruding portion in the hip holding portion.

* * * * *